(12) United States Patent
El Afandy et al.

(10) Patent No.: US 11,047,816 B2
(45) Date of Patent: Jun. 29, 2021

(54) HIGH RESOLUTION, NANOMEMBRANE-BASED, THERMAL DIFFUSIVITY BIOSENSOR FOR LIVING CELLS

(71) Applicant: KING ABDULLAH UNIVERSITY OF SCIENCE AND TECHNOLOGY, Thuwal (SA)

(72) Inventors: Rami Tarek El Afandy, Thuwal (SA); Boon Siew Ooi, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 279 days.

(21) Appl. No.: 16/068,012

(22) PCT Filed: Jan. 18, 2017

(86) PCT No.: PCT/IB2017/050269
§ 371 (c)(1),
(2) Date: Jul. 3, 2018

(87) PCT Pub. No.: WO2017/125866
PCT Pub. Date: Jul. 27, 2017

(65) Prior Publication Data
US 2019/0003994 A1    Jan. 3, 2019

Related U.S. Application Data

(60) Provisional application No. 62/280,224, filed on Jan. 19, 2016.

(51) Int. Cl.
*G01N 25/18* (2006.01)
*G01K 11/00* (2006.01)
(Continued)

(52) U.S. Cl.
CPC ............. *G01N 25/18* (2013.01); *G01K 11/00* (2013.01); *G01K 17/006* (2013.01); *G01N 21/62* (2013.01);
(Continued)

(58) Field of Classification Search
USPC ...... 374/29, 30, 44, 137, 121, 124, 161, 162
See application file for complete search history.

(56) References Cited

U.S. PATENT DOCUMENTS 5,030,012 A * 7/1991 Hagins .................. G01K 17/00
374/31
5,713,665 A * 2/1998 Kato ...................... G01N 25/18
374/43

(Continued)

OTHER PUBLICATIONS

International Search Report in related International Application No. PCT/IB2017/050269, dated Mar. 31, 2017.

(Continued)

*Primary Examiner* — Lisa M Caputo
*Assistant Examiner* — Nasir U. Ahmed
(74) *Attorney, Agent, or Firm* — Patent Portfolio Builders PLLC

(57) ABSTRACT

A method for measuring thermal diffusivity/conductivity of a microscale sample includes placing a metallic disk atop the sample, and disposing a nanomembrane over the sample and over the metallic disk so that the nanomembrane, so that the metallic disk, the nanomembrane and the sample are in thermal equilibrium with one another. A laser beam is directed to fall onto the nanomembrane over the sample, while a radiation sensor is operated to detect photoluminescent radiation emitted by the nanomembrane in response to the laser beam. A spectral shift in the detected photoluminescent radiation emitted by the nanomembrane is determined, and thermal diffusivity/conductivity is calculated from the determined spectral shift of the photoluminescence.

15 Claims, 3 Drawing Sheets

(51) Int. Cl.
| | |
|---|---|
| G01N 33/483 | (2006.01) |
| G01K 17/00 | (2006.01) |
| G01N 33/50 | (2006.01) |
| G01N 21/62 | (2006.01) |
| G01N 21/64 | (2006.01) |

(52) U.S. Cl.
CPC ......... *G01N 21/64* (2013.01); *G01N 33/4833* (2013.01); *G01N 33/5005* (2013.01); *G01N 21/6489* (2013.01)

(56) References Cited

U.S. PATENT DOCUMENTS

| | | | | |
|---|---|---|---|---|
| 7,407,325 | B2* | 8/2008 | Watanabe | G01N 25/18 374/121 |
| 2015/0328633 | A1* | 11/2015 | Yoo | B01L 3/502715 435/6.12 |

OTHER PUBLICATIONS

Park, B.Y., et al., "Thermal Conductivity of Single Biological Cells and Relation with Cell Viability," Applied Physics Letters, May 20, 2013, vol. 102, pp. 203702-1-203702-4.
Written Opinion of the International Searching Authority in related International Application No. PCT/IB2017/050269, dated Mar. 31, 2017.
Aksamija, Z., et al., "Anisotropy and boundary scattering in the lattice thermal conductivity of silicon nanomembranes," Physical Review B, vol. 82, 2010 (Published Jul. 27, 2010), pp. 045319-1-045319-7.
American Cancer Society, "Cancer Facts & Figures 2014," Annual Publication of the American Cancer Society, Atlanta, Georgia, 2014, pp. 1-70 (72 pages provided).
Antonakakis, T., et al., "Closed form solutions of the heat diffusion equation with a Gaussian source," International Journal of Heat and Mass Transfer, vol. 62, 2013 (Available online Apr. 9, 2013), pp. 314-322.
Chae, S.H., et al., "Transferred wrinkled Al2O3 for highly stretchable and transparent graphene-carbon nanotube transistors," Nature Materials, vol. 12, May 2013 (Published online Mar. 3, 2013; corrected online Mar. 8, 2013), pp. 403-409 (8 pages provided).
Chen, J., et al., "Gold Nanocages as Photothermal Transducers for Cancer Treatment," Small, vol. 6, No. 7, 2010 (Published online Mar. 11, 2010), pp. 811-817.
Choi, W.J., et al., "Full-field optical coherence microscopy for identifying live cancer cells by quantitative measurement of refractive index distribution," Optics Express, vol. 18, No. 22, Oct. 25, 2010 (Published Oct. 20, 2010), 11 pages.
Danilchenko, B.A., et al., "Heat capacity and phonon mean free path of wurtzite GaN," Applied Physics Letters, vol. 89, 2006 (Published online Aug. 7, 2006), pp. 061901-1-061901-3 (4 pages provided).
Duan, X., et al., "Intracellular recordings of action potentials by an extracellular nanoscale field-effect transistor," Nature Nanotechnology, vol. 7, Mar. 2012 (Published online Dec. 18, 2011), pp. 174-179.
Elafandy, R.T., et al., "Exfoliation of Threading Dislocation-Free, Single-Crystalline, Ultrathin Gallium Nitride Nanomembranes," Advanced Functional Materials, vol. 24, 2014 (Published online Dec. 19, 2013), pp. 2305-2311.
Elafandy, R.T., et al., "Nanomembrane-Based, Thermal-Transport Biosensor for Living Cells," Small, vol. 13, Article 1603080, 2017 (Published online Nov. 23, 2016), pp. 1-7 (cited in the International Search Report which is of record).
Guthy, C., et al., "Unusually low thermal conductivity of gallium nitride nanowires," Journal of Applied Physics, vol. 103, 2008 (Published online Mar. 28, 2008), pp. 064319-1-064319-8 (9 pages provided).

Habash, R.W.Y., et al., "Thermal Therapy, Part 2: Hyperthermia Techniques," Critical Reviews in Biomedical Engineering, vol. 34, No. 6, 2006, pp. 491-542.
Hanson, L., et al., "Vertical nanopillars for in situ probing of nuclear mechanics in adherent cells," Nature Nanotechnology, vol. 10, Jun. 2015 (Published online May 18, 2015), pp. 554-562 (10 pages provided).
Hénon, S., et al., "A New Determination of the Shear Modulus of the Human Erythrocyte Membrane Using Optical Tweezers," Biophysical Journal, vol. 76, Feb. 1999, pp. 1145-1151.
Jathoul, A.P., et al., "Deep in vivo photoacoustic imaging of mammalian tissues using a tyrosinase-based genetic reporter," Nature Photonics, vol. 9, Mar. 2015 (Published online Mar. 2, 2015), pp. 1-8 (9 pages provided).
Jewett, S.A., et al., "Gallium nitride is biocompatible and non-toxic before and after functionalization with peptides," Acta Biomaterialia, vol. 8, 2012 (Available online Oct. 7, 2011), pp. 728-733.
Klitsner, T., et al., "Phonon scattering at silicon crystal surfaces," Physical Review B, vol. 36, No. 12, Oct. 15, 1987, pp. 6551-6565.
Kovalev, D., et al., "Free exciton emission in GaN," Physical Review B, vol. 54, No. 4, Jul. 15, 1996, pp. 2518-2522.
Lee, J.-H., et al., "Exchange-coupled magnetic nanoparticles for efficient heat induction," Nature Nanotechnology, vol. 6, Jul. 2011 (Published online Jun. 26, 2011), pp. 418-422.
Li, B., et al., "Raman spectral study of silicon nanowires," Physical Review B, vol. 59, No. 3, Jan. 15, 1999, pp. 1645-1648.
Link, S., et al., "Shape and size dependence of radiative, non-radiative and photothermal properties of gold nanocrystals," International Reviews in Physical Chemistry, vol. 19, No. 3, Jul. 2000, pp. 409-453 (46 pages provided).
Mehlen, P., et al., "Metastasis: a question of life or death," Nature Reviews: Cancer, vol. 6, Jun. 2006, pp. 449-458.
Mei, Y., et al., "Fabrication, Self-Assembly, and Properties of Ultrathin AlN/GaN Porous Crystalline Nanomembranes: Tubes, Spirals, and Curved Sheets," ACS Nano, vol. 3, No. 7, 2009 (Published online Jun. 24, 2009), pp. 1663-1668.
Müller, T.J., et al., "Heat Transport Through a Biological Membrane—An Asymmetric Property? Technical Issues of Nonequilibrium Molecular Dynamics Methods," International Journal of Quantum Chemistry, vol. 111, No. 7/8, 2011 (Published online Aug. 19, 2010), pp. 1403-1418.
Nepal, N., et al., "Temperature and compositional dependence of the energy band gap of AlGaN alloys," Applied Physics Letters, vol. 87, 2005 (Published online Dec. 7, 2005), pp. 242104-1-242104-3 (4 pages provided).
Rogers, J.A., et al., "Synthesis, assembly and applications of semiconductor nanomembranes," Nature, vol. 477, Sep. 1, 2011, pp. 45-53.
Schroeder, A., et al., "Treating metastatic cancer with nanotechnology," Nature Reviews: Cancer, vol. 12, Jan. 2012, pp. 39-50 (13 pages provided).
Slack, G.A., et al., "Some effects of oxygen impurities on AlN and GaN," Journal of Crystal Growth, vol. 246, Dec. 2002, pp. 287-298.
Stonas, A.R., et al., "Development of selective lateral photoelectrochemical etching of InGaN/GaN for lift-off applications," Applied Physics Letters, vol. 78, No. 13, Mar. 26, 2001, pp. 1945-1947 (4 pages provided) (cited in the International Search Report which is of record).
Tiginyanu, I., et al., "Membrane-assisted revelation of the spatial nanoarchitecture of dislocation networks," Materials Letters, vol. 65, 2011 (Available online Oct. 20, 2010), pp. 360-362.
Viventi, J., et al., "A Conformal, Bio-Interfaced Class of Silicon Electronics for Mapping Cardiac Electrophysiology," Science Translational Medicine, vol. 2, Issue 24, Mar. 24, 2010, pp. 1-9 (11 pages provided).
Yu, X., et al., "Heat flow in proteins: Computation of thermal transport coefficients," The Journal of Chemical Physics, vol. 122, 2005 (Published online Jan. 14, 2005), pp. 054902-1-054902-11 (12 pages provided).
Zhang, H.F., et al., "Functional photoacoustic microscopy for high-resolution and noninvasive in vivo imaging," Nature Biotechnology, vol. 24, No. 7, Jul. 2006 (Published online Jun. 25, 2006), pp. 848-851.

(56) References Cited

OTHER PUBLICATIONS

Zharov, V.P., et al., "Photothermal Imaging of Nanoparticles and Cells," IEEE Journal of Selected Topics in Quantum Electronics, vol. 11, No. 4, Jul./Aug. 2005, pp. 733-751.

Zou, J., et al., "Thermal conductivity of GaN films: Effects of impurities and dislocations," Journal of Applied Physics, vol. 92, No. 5, Sep. 1, 2002, pp. 2534-2539 (7 pages provided).

* cited by examiner

HIGH RESOLUTION, NANOMEMBRANE-BASED, THERMAL DIFFUSIVITY BIOSENSOR FOR LIVING CELLS

CROSS-REFERENCE TO RELATED APPLICATIONS

This application is a U.S. National Stage Application of International Application No. PCT/IB2017/050269, filed on Jan. 18, 2017, which claims priority and benefit from U.S. Provisional Patent Application No. 62/280,224, filed Jan. 19, 2016, the entire contents of which are incorporated herein by reference.

BACKGROUND OF THE INVENTION

The present invention relates to a method for making high-resolution measurements of biological (and non biological) thermal diffusivity and thermal conductivity. The resolution is such that measurement of the thermal diffusivities/conductivities of individual biological cells is feasible (Resolution can also reach sub-cell resolution (cell organelles)). The present invention also relates to an associated biosensor. In addition, the present invention relates to an associated kit facilitating performance of the method.

With a 90% mortality rate, cancer metastasis, or the spread of cancerous cells from a primary tumor to seed secondary tumors, accounts for the majority of deaths among cancer patients[9,10]. Surgery, chemo-therapy and radiation-therapy, are ineffective in treating disseminated metastatic cells[5]; however recent progress in functionalized magnetic and plasmonic nanoparticles has led photothermal[3,4] and magneto-thermal[2] therapies to potentially target only cancerous cells throughout the body. Because the cellular response to overheating is highly dependent on both the temperature and the exposure time, and effects range from improved diffusion rate across the cellular membrane to irreversible damage and protein denaturation[11], precise information regarding the transient thermal energy distribution within the cell is required to efficiently target cancerous cells without affecting adjacent healthy cells. In addition to cancer therapies, several imaging techniques, such as photoacoustic[6,7] and photothermal[8] imaging, require the generation of confined heat pulses using pulsed laser sources. Thus, cellular thermal diffusivity, as a measure of the transient thermal response of a cell to a change in temperature, becomes a fundamental property to calculate the required exposure time and intensity based on the requirements of the applications. Although there are standard techniques for measuring thermal diffusivity, such as the transient plane or line sources and laser flashing methods, they currently lack the spatial resolution needed to measure diffusivity at the micron scale. Moreover, due to the irregular cellular curvilinear shapes, single-cell thermal diffusivity measurement requires a flexible sensor that is capable of following their contours.

SUMMARY OF THE INVENTION

The ability to manipulate low dimensional physics phenomena within nanostructures has always led to innovative techniques in determining physical properties of living cells, such as electrical[12], optical[13] and mechanical[14,15]. Among the different nanostructures, 2D nanostructures, such as nanomembranes (NMs), are unrivalled in their scalability for high-yield manufacture and, with the current transfer techniques, are less challenging in their manipulation compared with lower-dimensional nanostructures[16]. Furthermore, due to their extremely small flexural rigidity, NMs are highly flexible and can follow curvilinear surfaces[17,18]. The operation principle of our novel technique relies on the ability to spectrally shift the bandgap photoluminescence (PL) emission of gallium nitride (GaN) NMs through laser-induced heating due to the increased phonons-boundary-scattering rate. GaN NMs are just used for demonstration, other nanostructures or materials can be engineered to perform the same functionality.

A method for measuring thermal diffusivity comprises, in accordance with the present invention, (i) providing a microscale biological sample, (ii) placing a metallic disk atop the biological sample, (iii) disposing a nanomembrane over the biological sample and over the metallic disc so that the nanomembrane, the metallic disk and the biological sample are in thermal equilibrium with one another, (iv) directing a laser beam to fall onto the nanomembrane over the biological sample, (v) operating a radiation sensor to detect photoluminescent radiation emitted by the nanomembrane in response to the laser beam, (vi) determining a spectral shift in the detected photoluminescent radiation emitted by the nanomembrane, and (vii) calculating thermal diffusivity/conductivity from the determined spectral shift of the photoluminescence.

Pursuant to a feature of the invention, the metallic disk is pre-attached to the nanomembrane. The placing of the metallic disk and the disposing of the nanomembrane comprise positioning the nanomembrane and the metallic disk together atop the biological sample. Typically, the nanomembrane is provided with the metallic disk lying thereon, so that the method further contemplates flipping the nanomembrane so that the disk is underneath. The positioning of the nanomembrane and the metallic disk is performed after the flipping of the nanomembrane.

Another feature of the invention is without the usage of a metallic disk. In this case, the NM is formed from a material which can be excited with a wavelength that is not absorbed by the underlying biological (or non-organic) material.

Pursuant to another feature of the invention, a kit for use in making measurements of thermal diffusivity of microscale biological material comprises at least one nanomembrane having a maximum edge dimension in a microscale range and at least one metallic disk having a maximum dimension substantially less than a smallest dimension of the nanomembrane. The term "microscale" is used herein to denote sizes on the same order as that of living cells and clumps of cells. The nanomembranes are typically so small that a microscope is required to enable manipulation by a user.

The kit preferably comprises a plurality of nanomembranes each having a maximally sized edge dimension in a microscale range and further comprises a plurality of metallic disks each having a maximum dimension substantially less than a smallest dimension of each of the nanomembranes. Where the metallic disks are circular, they may have a diameter of between one half and one-twentieth that of an edge of a square nanomembrane.

The disks are preferably made of a material taken from the group consisting of gold, a gold alloy, platinum, and a platinum alloy, Aluminum, Silver (many of the metals will function at different wavelengths) and are each fastened to a respective one of the nanomembranes.

The present invention provides a method and apparatus for measuring single-cell thermal diffusivity. Here, the present approach of measuring the thermal diffusivity of single-cells has only a 2.2% error rate. We base our technique on increasing the diffusive phonon-boundary-scattering rate in nanomembranes to induce a considerable spectral dependence of the excitonic-bandgap emission over excitation-laser intensity. We further demonstrate that once in contact with organic or inorganic material, the nanomembranes' emission spectral-shift functions as an indicator of the material's thermal diffusivity. Due to the prior absence of a single-cell thermal diffusivity sensor, we anticipate our novel technique to enable an efficient single-cell targeting using nanoheaters, allow better modeling of thermal distribution within cells and potentially enable novel diagnostic techniques based on variations of single-cell thermal diffusivities.

BRIEF DESCRIPTION OF THE DRAWINGS

FIG. 2a is a band diagram of the photo-excited free-excitons in GaN showing laser excitation, phonon-assisted relaxation and PL emission. FIG. 2b is a schematic perspective view showing a nanomembrane disposed on a copper grid and exposed to a laser beam, to measure the laser-induced local heating. FIG. 2c is an optical image of the structure shown in FIG. 2b. FIG. 2d is a pair of graphs showing that, with increasing laser excitation intensity, PL signals measured from 40 and 10 nm thick GaN NMs exhibited spectral redshifts of different magnitudes because of the decrease of the thermal conductivity with NM thickness. FIG. 2e is a graph showing thermal conductivity simulation results of the laser-induced heating within the NMs. Circles, squares and triangles represent the mean measured peak emission energy from the 40, 20 and 10 nm thick NMs, respectively. The simulation results are indicated by solid black curves. An inset 3D plot shows the simulated steady-state heat distribution across the NM.

FIG. 3a is a schematic two-dimensional diagram of temperature distribution within a cell when the NM is in direct contact with the cell. FIG. 3b is a schematic two-dimensional diagram of temperature distribution within a cell when a 250 nm thick Au film is inserted under the NM. FIG. 3c is a schematic two-dimensional diagram of temperature distribution within a cell when the Au film is reduced to a 3 µm wide microdisk. The insertion of an Au film causes rapid lateral diffusion of the heat energy within the film. When the film is reduced to a disk, lateral heat diffusion is suppressed and heat diffuses vertically from the NM to the cell. FIG. 3d is a graph showing a simulated temperature depth profile for the three cases of FIGS. 3a-3c due to a 100 µs long excitation pulse, with the lowest curve corresponding to FIG. 3a (no gold), the middle curve corresponding to FIG. 3b (gold film) and the upper curve corresponding to FIG. 3c (gold microdisk). While the Au film caused a severe drop in the temperature, due to the enhanced lateral diffusion, temperature depth profile for the direct contact and the Au disk cases are similar. Ambient temperature was taken as 37° C. in these simulations.

FIG. 4a is an optical microscope image of the GaN NMs with the Au microdisk attached while resting on their original GaN substrate. FIG. 4b is an image showing a 10 µm wide tungsten tip used in picking up individual NMs from the GaN substrate, flipping them, transferring them to different materials. FIG. 4c shows an NM as transferred onto a substrate. With the NM facing downwards, the Au microdisk was sandwiched between the NM and the foreign substrate. FIG. 4d is an SEM micrograph of a cancer cell covered by a 35 nm thick NM. The micrograph is imaged under high KV mode to make the Au microdisk apparent in the image. FIG. 4e is a plot of the temperature difference ratios of the NM of several materials versus their thermal diffusivities (black dots). The solid curve is the same ratio constructed from the analytical solution to the heat diffusion equation 2. The positively sloped linear plot is the calculated measurement resolution.

DETAILED DESCRIPTION

Figure 1:
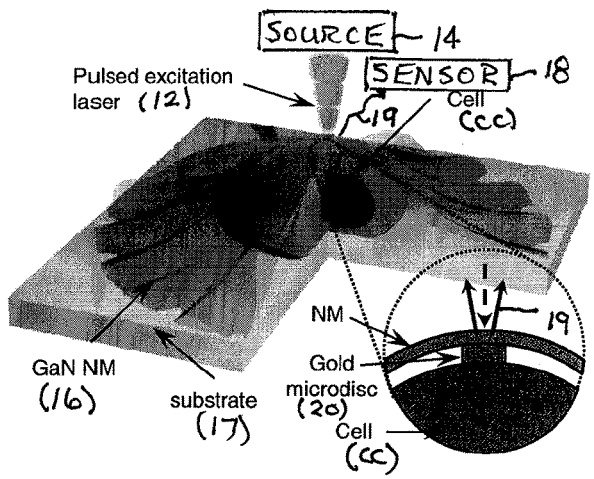
FIG. 1 is a schematic perspective view of a biosensor assembly for measuring single-cell thermal diffusivity. Schematic representation of a cell attached to a substrate and covered with a GaN NM. A laser beam is focused on the NM to induce local heating as well as PL emission. Because heat spontaneously diffuses from the NM to the cell, the temperature of the NM depends on the cell thermal diffusivity. Consequently, based on the measured temperature-dependent PL emission from the NM, we can estimate the cell thermal diffusivity. The magnified region represents the focused excitation beam (dashed arrow), which simulates spontaneous bandgap emission (straight solid arrows) as well as local heat energy which diffuses away from the source (zigzagged arrows).

As illustrated in FIG. 1, a pulsed, focused laser beam 12 from a laser source 14 locally heats a gallium nitride nanomembrane (NM) 16 that is in direct contact with a cancer cell CC disposed on a substrate 17. The generated heat energy spontaneously diffuses to the cancer cell CC at a rate proportional to the cell's thermal diffusivity. The temperature of the NM 16 thus depends on the cell's thermal diffusivity. A light sensor 18 such as a photocell or solid state camera (charge coupled device or CCD) detects photoluminescent (PL) light emission 19 from the nanomembrane NM. Knowledge of the nanomembrane's temperature, obtained by measuring the spectral-shift in its PL emission, yields information of the thermal diffusivity of the cancer cell CC. A gold microdisk 20 is disposed between and in thermal contact with the NM 16 and the cancer cell CC. The function of the gold (Au) microdisk 20 is to block unabsorbed laser radiation to prevent it from being absorbed within the underlying cell CC as further explained below. Because GaN is a robust, chemically stable and biocompatible[19] material we selected GaN material for the NM 16. Although fabrication of GaN NMs of different dimensions and crystalline properties has been demonstrated by several groups[20-22], there is no published work on employing their properties for biomedical applications.

Laser-Induced Heating in GaN NMs

Prior to demonstrating thermal diffusivity measurements of single-cells with the GaN NMs, it is imperative to study the effect of laser-induced local heating on the PL emission from NMs. Once excited by a 325 nm (3.81 eV) continuous-wave laser, photo-excited free-excitons emit a series of optical and acoustic phonons while relaxing towards their energy band minimum to conserve energy and momentum simultaneously (FIG. 2a)[23]. Thus, a local non-equilibrium density of phonons (a non-equilibrium temperature gradient) is established, causing the phonons to spontaneously diffuse away from the excitation region into the surrounding crystal. Due to its long phonon mean free path, or average distance travelled before scattering, ($\Lambda_{ph}$~100 nm)[24], GaN thermal conductivity is sufficiently high ($\kappa_{GaN}$=227 W/m·K)[25] which enables rapid phonon diffusion. Therefore, no steady-state local increase in temperature occurs, and the GaN PL peak emission energy (3.42 eV) exhibits no spectral dependence over increasing excitation laser intensity (up to 4.84 mW/μm²). Although phonon scattering in bulk GaN crystal at room temperature is dominated by Umklapp processes[26], once the crystal is reduced to a NM structure, with a thickness of less than $\Lambda_{ph}$, diffusive phonon-boundary-scattering becomes dominant and causes a reduction in $\Lambda_{ph}$ to approximately the NM thickness ($W_{NM}$)[27]. Consequently, the GaN NM thermal conductivity ($\Lambda_{NM} \propto \Lambda_{ph}$) significantly reduces as it scales down with $W_{NM}$[28]. Therefore, thermal energy is not dissipated rapid enough, and a steady-state increase in local temperature is established, which causes the GaN PL peak emission to redshift with increasing laser excitation intensity.

Figures 2A, 2B, 2C, 2D, 2E:
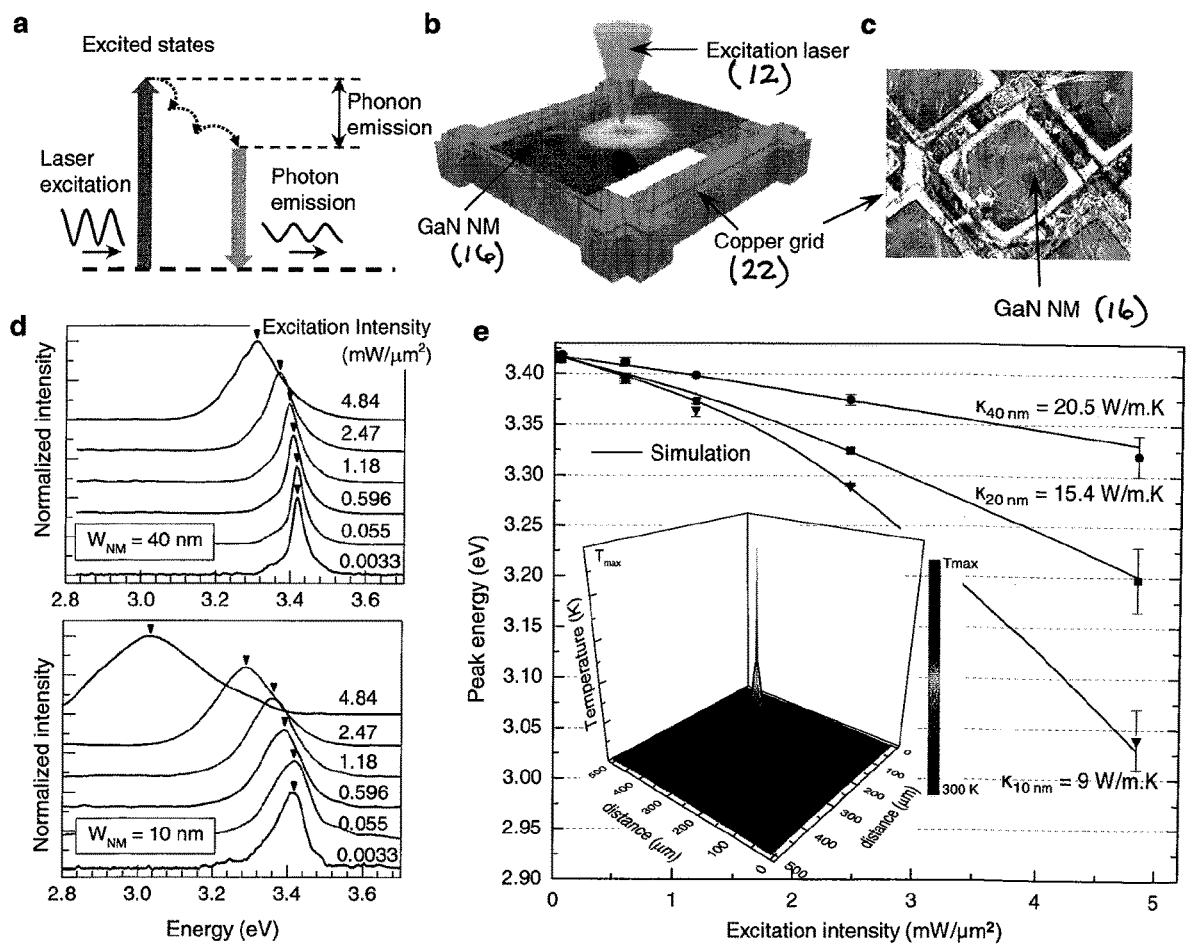
FIGS. 2a through 2e pertain to intensity-dependent PL emissions from NMs.

To measure the PL emission from the GaN NMs, we transferred the GaN NMs 16 to a copper grid 22, and focused a 325 nm laser beam 12 onto the NMs to a 3 μm spot size, as schematically presented in FIG. 2b and optically imaged in FIG. 2c. The normalized PL emissions from 40 and 10 nm thick GaN NMs at increasing laser excitation intensities were measured and plotted in FIG. 2d. At low-excitation intensity (3.3 μW/μm²), all NMs, regardless of thicknesses, emitted at the same energy (3.42 eV), indicating the absence of laser-induced local heating. However, at increasing excitation intensities, thinner NMs exhibited longer red-shifts as well as wider full width at half maximums (FWHMs), which is ascribed to an increase in the local temperature due to the increased probability of phonon-boundary-scattering[29,30].

To quantitatively estimate $\kappa_{NM}$ based on the spectral shift, we numerically solved the steady-state heat equation using MATLAB and then fitted the experimental data. Using the following equation:

$$-\kappa_{NM} W_{NM} \nabla^2 T + h_{tot}(T-T_a) + \epsilon\sigma_{SB}(T^4 - T_a^4) = Q_{exc}(x,y), \quad (1)$$

where T and $T_a$ are the NM and ambient temperatures, respectively. $h_{tot}$, ϵ and $\sigma_{SB}$ are the convection heat transfer coefficient, the GaN emissivity and the Stefan-Boltzmann constant, respectively. Finally, $Q_{exc}(x,y)$ is the heat generated within the NM due to excitation laser, modelled by a Gaussian distribution. The simulated steady-state heat distribution across the NM, plotted in the inset of FIG. 2e, indeed showed a steady-state accumulation of heat energy centred on the excitation laser spot. The PL emission energy from the NM was calculated from the local temperature based on Varshni's equation[31]. The mean measured peak emission energies were plotted with increasing excitation intensities in FIG. 2e for 40, 20 and 10 nm thick NMs, presented by circles, squares and triangles, respectively. $\kappa_{NM}$ of 20.5, 15.4 and 9 W/m·K gave the best simulation fit to the experimental data for the 40, 20 and 10 nm thick NMs, respectively.

Thermal Diffusivity Sensing Design

Figures 3A, 3B, 3C, 3D:
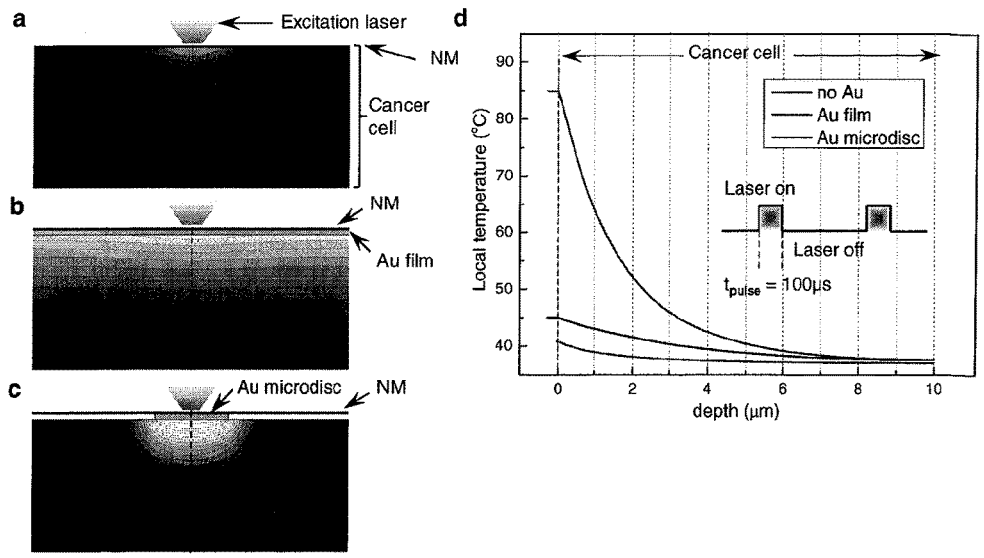
FIGS. 3a through 3d show COMSOL Multiphysics simulation results of the temperature profile due to a 100 µs long excitation laser pulse.

In our attempt to establish a solid theoretical foundation for our novel NM-based thermal diffusivity sensing technique, we first find an analytical solution to the heat diffusion equation. We simplified our NM/cell system to a semi-infinite homogenous medium which had an adiabatic surface and was heated by a Gaussian heat source. The rise in peak temperature at the heating source (at the NM) is then given by, $$\Delta T(t) = A \frac{\sigma^2}{\kappa_{cell}} \times \left( \frac{1}{\sigma} - \frac{1}{\sqrt{\sigma^2 + 2\alpha_{cell} t}} \right), \quad (2)$$

where A and σ are the Gaussian heat source (laser) amplitude and standard deviation, respectively; $\kappa_{cell}$ and $\alpha_{cell}$ n are the cell thermal conductivity and diffusivity, respectively; and t represents the heating time[32]. It is apparent from the above solution that the NM emission, as a function of ΔT, depends on both $\kappa_{cell}$ and $\alpha_{cell}$ which should not be the case for a thermal diffusivity measurement technique. However, the ratio of the temperature changes due to different heating periods, $R_{t_1/t_2} = \Delta T(t_1)/\Delta T(t_2)$, cancels the time-independent term outside the bracket and is only a function of $\alpha_{cell}$. Thus, instead of using a continuous laser source, the laser was pulsed at two different time periods ($t_1$ and $t_2$), and the ratio between the rise in local temperatures was calculated. This technique also allowed the measurement to be independent from the laser amplitude, which yielded a more controlled experiment. FIG. 3a shows the COMSOL Multiphysics simulation results of the heat diffusion equation within the NM/cell system due to a 100 μs long laser pulse, with the temperature depth profile plotted in FIG. 3b. As demonstrated from the depth profile, a 100 μs long pulse width limited the heat diffusion to within the cell boundaries, thus allowing for the infinite medium approximation.

Because the NM thickness used in this study (35 nm) was much less than the penetration depth of 325 nm radiation in GaN (~85 nm), approximately 50% of the optical energy was transmitted through the NM. This transmitted energy, depending on the underlying cell's optical properties, was absorbed, transmitted or reflected back to the NM. Therefore, the generated heat energy, and hence the observed PL energy shift, became functions of the cell's optical properties. To address this issue, we inserted a 250 nm thin layer of Au under the NM to prevent UV radiation from reaching the cancer cell, while at the same time, due to its high thermal diffusivity (170 mm²/s), does not interfere with heat diffusion from the NM to the cancer cell. Unfortunately, as demonstrated by the simulation results (FIG. 3b and FIG. 3d), the insertion of an Au film significantly enhanced lateral thermal diffusion, which delocalized the generated heat energy and rendered the measurements prone to boundary effects (such as cell dimensions and surrounding medium). To suppress lateral thermal diffusion, the Au film was reduced to a 4 μm wide microdisk (FIG. 3c). The modified temperature profile became similar to the direct contact case with a considerable increase in temperature due to the absorbed laser energy within the Au microdisk.

Thermal Diffusivity Measurement

Figures 4A, 4B, 4C, 4D, 4E:
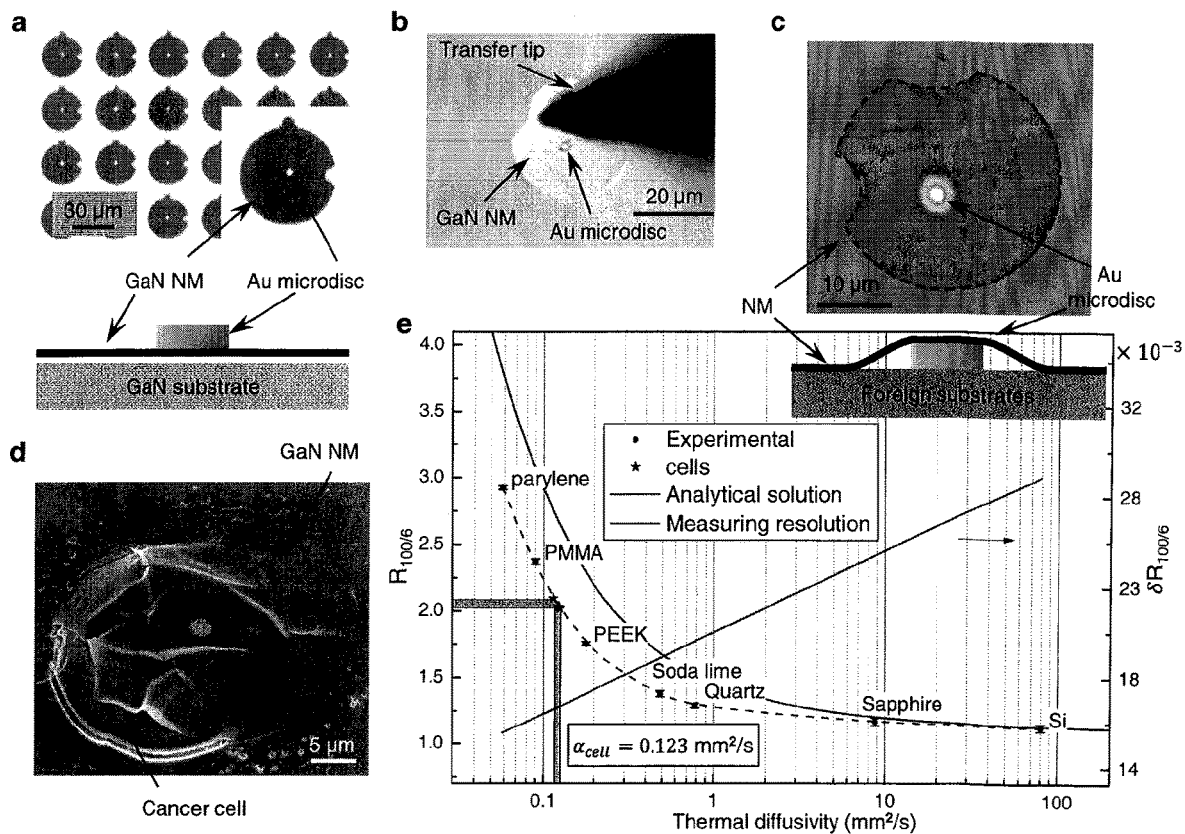
FIGS. 4a through 4e show experimental measurements of thermal diffusivity.

To verify the ability of the described experimental design to measure thermal diffusivity, we first transferred the NMs to several materials of known thermal diffusivities ($\alpha_{material}$) and recorded $R_{t_1/t_2}$. Through several lithography, metal evaporation and plasma etching techniques, we fabricated 40 μm wide, 35 nm thick GaN NMs with 3 μm wide, 250 nm thick Au microdisks attached to them (FIG. 4a and Methods). With the aid of a 10 μm tungsten tip attached to a micrometre probe positioner, we picked up the NMs (FIG. 4b), flipped them (so that the Au microdisk is facing down) and transferred them to several materials with different $\alpha_{material}$ (FIG. 4c). To eliminate any structural or morphological variations within the NMs and the attached Au microdisks, which would induce errors within the measurements, we only transferred adjacent NMs from an area of 0.5×0.5 mm². A 325 nm pulsed laser was focused onto the Au microdisk and the PL emission was measured at increasing laser intensities. The increase in the NM local temperature was then calculated from the PL shift using Varshni's equation. Finally, the measurement was repeated at two different laser pulse widths (100 and 6 μs), and $R_{100/6}$ was calculated for the NMs on the different materials ($R_{100/6}$ is plotted versus $\alpha_{material}$ FIG. 4e). The solid hyperbolic curve in FIG. 4e represents the analytical solution (equation 2) using the current experimental conditions (Methods). Although, similar dependence of $R_{100/6}$ over $\alpha_{material}$ is observed at both the experimental and analytical solutions, higher $R_{100/6}$ values are analytically calculated than experimentally measured at lower $\alpha_{material}$. This discrepancy arose because the analytical solution did not account any heat loss from the NM surface, whether convection or radiation.

Next we demonstrate the applicability of our technique to biological cells. First, we constructed a calibration curve (FIG. 4e) from the experimental data to estimate $\alpha_{cell}$ given $R_{100,6}$. We observe a clear nonlinearity in the sensitivity of our measuring technique, given by the slope of the calibration curve ($\delta R_{t_1,t_2}/\delta\alpha$, where δ denotes the minimum resolution of the quantity), with the sensitivity improving with decreasing $\alpha_{material}$. We then plated an MCF-7 breast cancer cell line onto a glass slide (Methods), and with the aid of a tungsten tip, we performed multiple transfers of NMs on top of several cells (FIG. 4d). From several cells of the same cell line, we measured an average $R_{100/6}$ equal to 2.05, which yielded $\alpha_{cell}$ equal to 0.123 mm²/s. Interestingly, the measured $\alpha_{cell}$ was slightly less than that of water (0.143 mm²/s), which is consistent with the fact that water normally accounts for approximately 80% of the cell's weight. Furthermore, the water content within living cells harbors a large composition of macromolecules, such as proteins, having calculated thermal conductivities less than water[33,34], thereby contributing to a lower thermal conductivity of living cells[35].

The measurement resolution of our thermal diffusivity measuring technique (δα) is limited by experimental setup as well as by measured sample properties. Over the range of 3.33 eV to 3.42 eV, the average spectral resolution of the 2400 lines grating ($\delta E_{GR}$) used in the above measurements is 0.137 meV, which yields a value of 0.25° C. for δT. Because $\delta R_{t_1,t_2} = R_{t_1,t_2}\sqrt{(\delta T/\Delta T_1)^2+(\delta T/\Delta T_2)^2}$, we observe that higher temperature shifts, which depend on $\kappa_{material}$, $A_{laser}$ and $\sigma_{laser}$, result in smaller $\delta R_{t_1,t_2}$. Based on the optics and materials used, we plot the calculated $\delta R_{t_1,t_2}$ (FIG. 4e). As $\alpha_{material}$ decreases, $\delta R_{t_1,t_2}$ decreases from 0.026 (for silicon) to 0.014 (for parylene) with a value of 0.019 for the MFC-7 cancer cells. Using $\delta R_{t_1,t_2}/\delta\alpha$, we obtain $\delta\alpha_{cell}$=0.0026 mm²/s, which is only 2.2% of the measured $\alpha_{cell}$. Increasing the laser intensity or the pulse width lowers this error but on the expense of generating more heat which will affect the cancer cells. On the other hand, using materials with optical emissions which have higher spectral dependence over temperature than GaN, will increase the measuring resolution of the technique.

In conclusion, we developed a novel thermal diffusivity measuring technique based on the transient response of GaN NMs to laser-induced heating. We also successfully measured, for the first time, the thermal diffusivity of cancerous cells to enable high-precision single-cell targeting using nanoparticles based hyperthermia treatment. Moreover, measuring the thermal diffusivities yields a more controllable experimental design for therapeutic or imaging techniques dealing with transient temperature variations within the cells. While we measured diffusivity for single cells, the spatial resolution can be increased or decreased, with a shorter or longer pulse width, respectively, to measure the diffusivity of subcellular regions or cell clusters and whole tissues. Finally, as demonstrated, the presented technique is not limited to biomedical applications and can also be employed in non-biological samples.

Methods

NM fabrication. Using a VEECO GEN930 plasma-assisted molecular beam epitaxy (PAMBE) system, a 35 nm thick indium gallium nitride (InGaN) sacrificial layer was grown at 560° C., followed by 40 nm thick GaN grown at 640° C., on a 500 nm GaN on a sapphire template wafer. The wafer was then cleaved into 1 cm² pieces, which were subsequently degreased in acetone and isopropanol (IPA) for κ mins and then cleaned in nitric acid ($HNO_3$) at 65° C. for 15 mins for surface oxide removal. A thin layer of platinum metal (150 nm) was then deposited near the edge of the top surface. Finally, a layer of AZ resist was spin-coated and patterned into 40 μm wide disks, followed by inductively coupled plasma (ICP) reactive ion etching (RIE) using an Argon (Ar)/Chlorine (Cl)-based recipe to expose the InGaN sacrificial layer. The remaining photoresist was then removed with acetone, and the sample was cleaned in IPA.

Au microdisk fabrication. A 250 nm thick layer of Au was evaporated onto the sample, followed by a spin-coated layer of SU8-2000.5 photoresist which was then patterned into 4 μm disks. Using Ar-bombardment in an ICP reactor, 150 nm of Au was removed, followed by 10 seconds immersion in potassium iodide (KI)/iodine ($I_2$) based Au etchant to etch away the remaining 100 nm, leaving behind the intact GaN structure. Finally, oxygen ($O_2$) plasma was used to remove the remaining SU-8 photoresist.

NM exfoliation. The samples were immersed in a bath containing $CH_3OH:H_2O_2(35\%):HF(48\%)$ (1:2:2). Back light illumination was performed by focusing light coming from a 200 W mercury (Hg) arc lamp onto the sample. To selectively etch the InGaN sacrificial layer, any photon energies higher than the GaN bandgap was blocked by placing a polished GaN wafer on top of the etching bath[36]. Once the InGaN was completely etched, the samples were gently cleaned by dipping them in IPA and were then dried using a critical point dryer (CPD) to enable proper exfoliation of the NM.

PL measurement. The PL emission from the NM was measured by focusing radiation from a helium-cadmium (He—Cd) gas laser to an average spot of 3 μm in diameter. The PL signal was then collected and sent to a 2400 line diffraction grating for dispersion. We pulsed the laser by passing the beam through a high-speed chopper.

Cell culture. Breast cancer cell lines (MCF-7) were purchased from ATCC (Manassas, Va., USA). The MCF-7 cells were cultured in MEM medium supplemented with 10% foetal bovine serum (FBS) and Penicillin/Streptomycin solution (100 units/ml penicillin, 100 μg/ml streptomycin) and maintained in a humidified incubator at 37° C. and 5% $CO_2$. In all assays, the cells used were from passages 5-25 and were used in suspension or plated on a glass slide (Fisher Scientific Ltd, UK) pre-coated with attachment factor protein (1×; Fisher Scientific Ltd, UK) for 30 minutes at 37° C. Finally, the MCF-7 cells were seeded at a density of 3×10⁵ cells/mL (9×10⁴ cells/cm²) and incubated at 37° C. and 5% $CO_2$ in a humidified incubator for 24 hours before transferring the NMs onto the cells.

COMSOL Multiphysics simulation. The cell was modelled as a cylinder with a 5 μm radius and a 10 μm height. Because water normally accounts for approximately 80% of the cell's weight, we used water thermal conductivity and diffusivity to model the thermal properties of living cells. Because cells have even lower thermal diffusivities than water, heat energy will be further confined in case of cells. Regarding the thermal properties of gallium nitride (GaN) and gold (Au), we used the values available in the COMSOL libraries. The following time-dependent heat diffusion equation was solved for the NM/Au microdisk/cell system:

$$\frac{\partial T}{\partial t} + \nabla T = \nabla \cdot (u \nabla T) + \frac{Q}{\rho C_p}$$

where $\alpha$, $\rho$, $C_p$ and Q are the thermal diffusivity, density, specific heat capacity at constant pressure and heat source power per unit volume, respectively. The initial temperature was set at 37° C. Convection cooling from the NM is taken into account by having a column of air on the NM.

Figure 5:
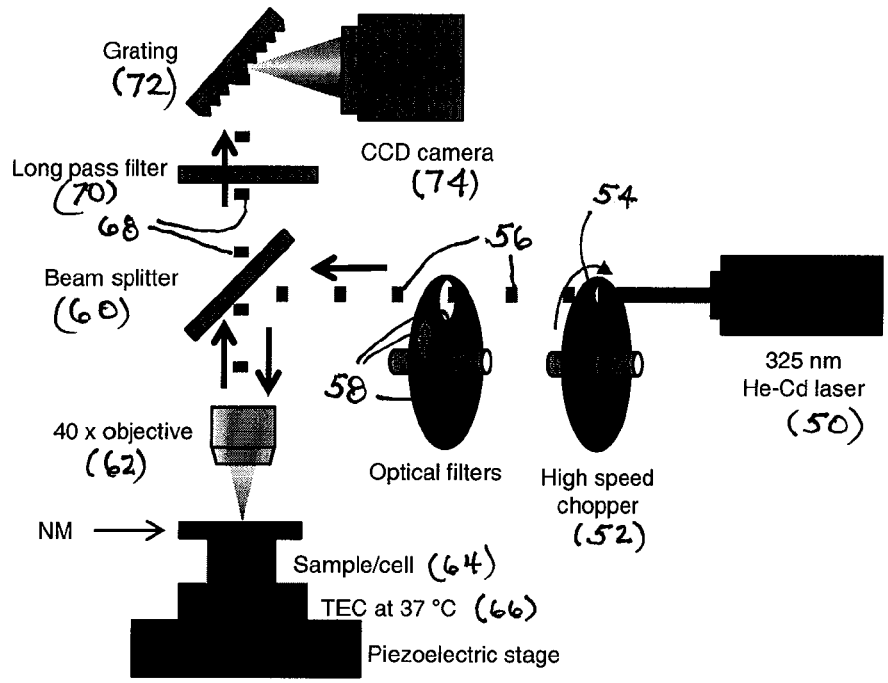
FIG. 5 is a diagram of an experimental setup used to measure thermal diffusivities. The diagram depicts an beam optical path for an excitation 325 nm laser as well as PL emission from target NMs.
Figure 6:
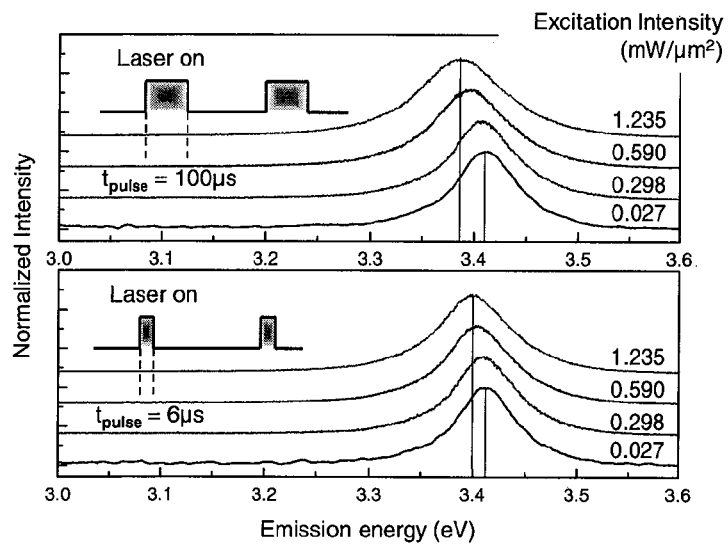
FIG. 6 is a pair of graphs showing PL emission from a nanomembrane attached to a cell. Collected PL emissions from a single NM attached to a cell at an increasing laser excitation intensity for long (top graph) and short (bottom graph) pulse widths.

Experimental optical setup. As shown in FIG. 5, 325 nm laser radiation, originating from a helium-cadmium (He—Cd) laser 50, was first chopped into 6 μs or 100 μs pulses using a Scitec 310CD high-speed optical chopper 52 with an in-house drilled 400 μm wide hole 54. The generated pulses 56 had a very low duty cycle ($1.27 \times 10^{-3}$) to ensure that all of the laser-generated heat energy during one pulse is dissipated before the incoming second heating pulse. A set of optical density filters 58 were used to vary the laser radiation intensity from 0.027 to 1.235 mW/μm². After locating the Au microdisk (not shown), which is attached to the NM 58, the laser beam pulses 56 were reflected by a beam splitter 60 and focused to a spot of 3 μm in diameter using a 40× UV objective lens 62. The sample 64 was left on a thermo-electric controller 66, set at 37° C., long enough to reach thermal equilibrium prior to performing the measurement. The photoluminescence emission 68 from the NM 58, was then collected by the same objective 62, transmitted through the beam splitter 60, filtered at 70 and dispersed by a 2400 line grating 72 onto a charge-coupled device (CCD) camera 74. Each measurement consisted of collecting the PL emission at different laser radiation intensities and different chopping speeds.

Materials Used for Calibration

Prior to measuring the thermal diffusivities of cells, we transferred the NMs onto materials of known thermal diffusivities to calibrate the measured signal. Because the fabrication/growth procedure of any material affects its final thermal diffusivity, we could not rely on standard available thermal diffusivities and had to measure the thermal diffusivities ourselves. The measured thermal diffusivities of the materials, which were measured using laser flash technique, are listed in Table 1.

TABLE 1

| Material | Thermal diffusivity (mm²/s) |
| --- | --- |
| Parylene | 0.0588 |
| Poly(methyl methacrylate) (PMMA) | 0.09 |
| Polyether ether ketone (PEEK) | 0.178 |
| Soda-lime glass | 0.487 |
| Quartz | 0.78 |
| Sapphire | 8.77 |
| Silicon | 80 |

Heating Curves of a Single Cell

FIG. 10 shows a sample of the measured PL emissions from NMs on cells. At both long (100 μs) and short (6 μs) pulse widths, the PL emission from the NM attached to the cancer cell emitted at the same peak emission when the excitation intensity was 0.027 mW/μm². As the excitation intensity increased, the PL emission from the NM got spectrally redshifted due to the laser-induced heating. As observed, the redshift was higher for a 100 μs pulse width than a 6 μs pulse. We then converted the energy shifts into temperature shifts (using Varshni's equation). Finally, the ratio between the two shifts was calculated and used to estimate the thermal diffusivities (using the calibration curve constructed above, FIG. 4).

REFERENCES

1 Steeg, P. S. Tumor metastasis: mechanistic insights and clinical challenges. Nat Med 12, 895-904 (2006).
2 Lee, J.-H. et al. Exchange-coupled magnetic nanoparticles for efficient heat induction. Nat Nano 6, 418-422, doi: 10.1038/nnano.2011.95 (2011).
3 Chen, J. et al. Gold Nanocages as Photothermal Transducers for Cancer Treatment. Small 6, 811-817, doi: 10.1002/smll.200902216 (2010).
4 Stephan Link, M. A. E.-S. Shape and size dependence of radiative, non-radiative and photothermal properties of gold nanocrystals. International Reviews in Physical Chemistry 19, 409-453, doi:10.1080/01442350050034180 (2010).
5 Schroeder, A. et al. Treating metastatic cancer with nanotechnology. Nat Rev Cancer 12, 39-50 (2012).
6 Zhang, H. F., Maslov, K., Stoica, G. & Wang, L. V. Functional photoacoustic microscopy for high-resolution and noninvasive in vivo imaging. Nat Biotech 24, 848-851, doi:10.1038/nbt1220 (2006).
7 Jathoul, A. P. et al. Deep in vivo photoacoustic imaging of mammalian tissues using a tyrosinase-based genetic reporter. Nat Photon 9, 239-246, doi:10.1038/nphoton.2015.22 (2015).
8 Zharov, V. P. & Lapotko, D. O. Photothermal imaging of nanoparticles and cells. Selected Topics in Quantum Electronics, IEEE Journal of 11, 7033-751, doi:10.1109/JSTQE.2005.857382 (2005).
9 Mehlen, P. & Puisieux, A. Metastasis: a question of life or death. Nat Rev Cancer 6, 449-458 (2006).
10 Society, A. C. Cancer Facts & FIGS. 2014. Atlanta: American Cancer Society (2014).
11 Habash, R. W. Y., Bansal, R., Krewski, D. & Alhafid, H. T. Thermal Therapy, Part 2: Hyperthermia Techniques. Critical Reviews in Biomedical Engineering 34, 491-542, doi:10.1615/CritRevBiomedEng.v34.i6.30 (2006).
12 Duan, X. et al. Intracellular recordings of action potentials by an extracellular nanoscale field-effect transistor. Nat Nano 7, 174-179, doi:10.1038/nnano.2011.223 (2012).
13 Choi, W. J. et al. Full-field optical coherence microscopy for identifying live cancer cells by quantitative measurement of refractive index distribution. Opt. Express 18, 23285-23295, doi:10.1364/OE.18.023285 (2010).
14 Hénon, S., Lenormand, G., Richert, A. & Gallet, F. A new determination of the shear modulus of the human erythrocyte membrane using optical tweezers. Biophysical Journal 76, 1145-1151 (1999).
15 Hanson, L. et al. Vertical nanopillars for in situ probing of nuclear mechanics in adherent cells. Nat Nano 10, 554-562, doi:10.1038/nnano.2015.88 (2015).

16 Rogers, J., Lagally, M. & Nuzzo, R. Synthesis, assembly and applications of semiconductor nanomembranes. *Nature* 477, 45-53 (2011).

17 Viventi, J. et al. A Conformal, Bio-Interfaced Class of Silicon Electronics for Mapping Cardiac Electrophysiology. *Science Translational Medicine* 2, 24ra22-24ra22, doi:10.1126/scitranslmed.3000738 (2010).

18 Chae, S. H. et al. Transferred wrinkled Al2O3 for highly stretchable and transparent graphene-carbon nanotube transistors. *Nature Materials* (2013).

19 Jewett, S. A., Makowski, M. S., Andrews, B., Manfra, M. J. & Ivanisevic, A. Gallium nitride is biocompatible and non-toxic before and after functionalization with peptides. *Acta Biomaterialia* 8, 728-733, doi:10.1016/j.actbio.2011.09.038 (2012).

20 Mei, Y. et al. Fabrication, Self-Assembly, and Properties of Ultrathin AlN/GaN Porous Crystalline Nanomembranes: Tubes, Spirals, and Curved Sheets. *ACS Nano* 3, 1663-1668, doi:10.1021/nn900580j (2009).

21 ElAfandy, R. T. et al. Exfoliation of Threading Dislocation-Free, Single-Crystalline, Ultrathin Gallium Nitride Nanomembranes. *Advanced Functional Materials* 24, 2305-2311, doi:10.1002/adfm.201303001 (2014).

22 Tiginyanu, I., Popa, V. & Stevens-Kalceff, M. A. Membrane-assisted revelation of the spatial nanoarchitecture of dislocation networks. *Materials Letters* 65, 360-362, doi:10.1016/j.matlet.2010.10.033 (2011).

23 Kovalev, D. et al. Free exciton emission in GaN. *Physical Review B* 54, 2518-2522 (1996).

24 Danilchenko, B. A., Paszkiewicz, T., Wolski, S., Jezowski, A. & Plackowski, T. Heat capacity and phonon mean free path of wurtzite GaN. *Applied Physics Letters* 89, 061901, doi:10.1063/1.2335373 (2006).

25 Slack, G. A., Schowalter, L. J., Morelli, D. & Freitas Jr, J. A. Some effects of oxygen impurities on AlN and GaN. *Journal of Crystal Growth* 246, 287-298, doi:10.1016/S0022-0248(02)01753-0 (2002).

26 Zou, J., Kotchetkov, D., Balandin, A. A., Florescu, D. I. & Pollak, F. H. Thermal conductivity of GaN films: Effects of impurities and dislocations. *Journal of Applied Physics* 92, 2534-2539, doi:10.1063/1.1497704 (2002).

27 Aksamija, Z. & Knezevic, I. Anisotropy and boundary scattering in the lattice thermal conductivity of silicon nanomembranes. *Physical Review B* 82, 045319 (2010).

28 Klitsner, T. & Pohl, R. O. Phonon scattering at silicon crystal surfaces. *Physical Review B* 36, 6551-6565 (1987).

29 Guthy, C., Nam, C.-Y. & Fischer, J. E. Unusually low thermal conductivity of gallium nitride nanowires. *Journal of Applied Physics* 103, 064319, doi:10.1063/1.2894907 (2008).

30 Piscanec, S. et al. Raman spectroscopy of silicon nanowires. *Physical Review B* 68, 241312 (2003).

31 Nepal, N., Li, J., Nakarmi, M. L., Lin, J. Y. & Jiang, H. X. Temperature and compositional dependence of the energy band gap of AlGaN alloys. *Applied Physics Letters* 87, -, doi:10.1063/1.2142333 (2005).

32 Antonakakis, T., Maglioni, C. & Vlachoudis, V. Closed form solutions of the heat diffusion equation with a Gaussian source. *International Journal of Heat and Mass Transfer* 62, 314-322, doi:10.1016/j.ijheatmasstransfer.2013.02.061 (2013).

33 Müller, T. J. & Müller-Plathe, F. Heat transport through a biological membrane—An asymmetric property? Technical issues of nonequilibrium molecular dynamics methods. *International Journal of Quantum Chemistry* 111, 1403-1418, doi:10.1002/qua.22785 (2011).

34 Yu, X. & Leitner, D. M. Heat flow in proteins: Computation of thermal transport coefficients. *The Journal of Chemical Physics* 122, 054902, doi:10.1063/1.1830431 (2005).

35 Kyoo Park, B., Yi, N., Park, J. & Kim, D. Thermal conductivity of single biological cells and relation with cell viability. *Applied Physics Letters* 102, -, doi:10.1063/1.4807471 (2013).

36 Stonas, A. R., Margalith, T., DenBaars, S. P., Coldren, L. A. & Hu, E. L. Development of selective lateral photoelectrochemical etching of InGaN/GaN for lift-off applications. *Applied Physics Letters* 78, 1945, doi:10.1063/1.1352663 (2001).

What is claimed is:

1. A method for calculating a thermal diffusivity of a microscale biological sample, the method comprising:
   providing the microscale biological sample;
   placing a metallic disk atop the biological sample;
   disposing a nanomembrane over the biological sample and over the metallic disk so that the nanomembrane, the metallic disk and the biological sample are in thermal equilibrium with one another;
   directing a laser beam to fail onto the nanomembrane over the biological sample;
   operating a radiation sensor to detect photoluminescent radiation emitted by the nanomembrane in response to the laser beam;
   determining a spectral shift in the detected photoluminescent radiation emitted by the nanomembrane; and
   calculating a thermal diffusivity of the biological sample from the determined spectral shift of the photoluminescence radiation emitted by the nanomembrane.

2. The method defined in claim 1, wherein the metallic disk is attached to the nanomembrane, the placing of the metallic disk and the disposing of the nanomembrane comprising positioning the nanomembrane and the metallic disk together atop the biological sample.

3. The method defined in claim 2, further comprising:
   providing the nanomembrane with the metallic disk lying thereon, flipping the nanomembrane so that the disk is underneath, the positioning of the nanomembrane and the metallic disk being performed after the flipping of the nanomembrane.

4. The method defined in claim 1, further comprising:
   pulsing a laser source with first and second time periods and measuring a rise in temperature of the nanomembrane due to each time period.

5. The method defined in claim 4, further comprising:
   calculating a ratio between the rise of the temperature of the nanomembrane due to the first and second time periods to obtain a parameter that is independent from the laser beam's amplitude.

6. The method defined in claim 5, wherein the thermal diffusivity of the biological sample is proportional to the ratio between the rise of the temperature of the nanomembrane due to the first and second time periods.

7. A method for measuring a thermal diffusivity, comprising:
   providing a microscale sample;
   disposing a nanomembrane over the sample so that the nanomembrane and the sample are in thermal equilibrium with one another;
   directing a laser beam to fall onto the nanomembrane over the sample;
   operating a radiation sensor to detect photoluminescent radiation emitted by the nanomembrane in response to the laser beam;

determining a spectral shift in the detected photoluminescent radiation emitted by the nanomembrane; and
calculating thermal diffusivity from the determined spectral shift of the photoluminescence.

8. The method defined in claim 7, further comprising placing a metallic disk between the nanomembrane and the sample prior to the directing of the laser beam to fall on the sample.

9. The method defined in claim 8, wherein the metallic disk is attached to the nanomembrane, the placing of the metallic disk and the disposing of the nanomembrane comprising positioning the nanomembrane and the metallic disk together atop the sample.

10. The method defined in claim 9, further comprising:
providing the nanomembrane with the metallic disk lying thereon, flipping the nanomembrane so that the disk is underneath, the positioning of the nanomembrane and the metallic disk being performed after the flipping of the nanomembrane.

11. The method defined in claim 8, wherein said disk is made of a material taken from the group consisting of gold, platinum, silver, aluminum and alloys thereof.

12. The method defined in claim 8, wherein said disk is attached to said nanomembrane prior to the disposing a nanomembrane over the sample.

13. The method defined in claim 7, further comprising:
pulsing a laser source with first and second time periods and measuring a rise in temperature of the nanomembrane due to each time period.

14. The method defined in claim 13, further comprising:
calculating a ratio between the rise of the temperature of the nanomembrane due to the first and second time periods to obtain a parameter that is independent from the laser beam's amplitude.

15. The method defined in claim 14, wherein the thermal diffusivity of the biological sample is proportional to the ratio between the rise of the temperature of the nanomembrane due to the first and second time periods.

* * * * *